US005574179A

United States Patent [19]

Wahl et al.

[11] Patent Number: 5,574,179

[45] Date of Patent: Nov. 12, 1996

[54] CONCENTRATED BIODEGRADABLE QUATERNARY AMMONIUM FABRIC SOFTENER COMPOSITIONS AND COMPOUDS CONTAINING INTERMEDIATE IODINE VALUE UNSATURATED FATTY ACID CHAINS

[75] Inventors: Errol H. Wahl, Cincinnati; Dennis R. Bacon, Milford; Ellen S. Baker, Cincinnati, all of Ohio; Jean-Francois Bodet, Newcastle Upon Tyne, Great Britain; Michael E. Burns, West Chester, Ohio; Hugo J. M. Demeyere, Merchtem, Belgium; Charles A. Hensley; Robert Mermelstein, both of Cincinnati, Ohio; John C. Severns, West Chester, Ohio; John H. Shaw, Jr.; Michael P. Siklosi, both of Cincinnati, Ohio; Alice M. Vogel, West Chester, Ohio; Jeffrey W. Watson, Cincinnati, Ohio

[73] Assignee: The Procter & Gamble Company, Cincinnati, Ohio

[21] Appl. No.: 395,263

[22] Filed: Feb. 28, 1995

Related U.S. Application Data

[60] Division of Ser. No. 142,739, Oct. 25, 1993, abandoned, which is a continuation-in-part of Ser. No. 24,541, Mar. 1, 1993, abandoned.

[51] Int. Cl.$^{6}$ .................................................. C07C 101/00

[52] U.S. Cl. .......................... 554/110; 554/103; 554/108; 554/109; 564/281; 564/291

[58] Field of Search .................................... 554/103, 108, 554/109, 110; 564/281, 291

[56] References Cited

U.S. PATENT DOCUMENTS

| | | | |
|---|---|---|---|
| 4,137,180 | 1/1979 | Naik et al. | 252/8.8 |
| 4,454,049 | 6/1984 | MacGilp et al. | 252/8.8 |
| 4,456,554 | 6/1984 | Walz et al. | 260/403 |
| 4,767,547 | 8/1988 | Straathof et al. | 252/8.8 |
| 4,789,491 | 12/1988 | Chang et al. | 252/8.75 |
| 4,844,823 | 7/1989 | Jacques et al. | 252/8.8 |
| 4,923,642 | 5/1990 | Rutzen et al. | 260/404 |
| 5,066,414 | 11/1991 | Chang | 252/8.8 |

FOREIGN PATENT DOCUMENTS

| | | | |
|---|---|---|---|
| 122140A2 | 4/1983 | European Pat. Off. | C11D 1/62 |
| 0079746A2 | 5/1983 | European Pat. Off. | C11D 1/835 |
| 0122141A2 | 10/1984 | European Pat. Off. | C11D 1/162 |
| 240727A2 | 10/1987 | European Pat. Off. | C11D 10/04 |
| 370675A2 | 5/1990 | European Pat. Off. | C11D 1/62 |
| 0404471 | 12/1990 | European Pat. Off. | C11D 3/00 |
| 0409502A2 | 1/1991 | European Pat. Off. | C11D 1/62 |
| 0409504A2 | 1/1991 | European Pat. Off. | C11D 1/65 |
| 0479608A2 | 4/1992 | European Pat. Off. | C11D 3/00 |
| 0507478A1 | 10/1992 | European Pat. Off. | C11D 1/835 |
| 3904754A1 | 8/1989 | Germany | D06M 13/46 |
| 4015849A | 11/1991 | Germany | C07C 219/08 |
| 63-223099 | 9/1988 | Japan | C11D 10/02 |
| 1-229877 | 9/1989 | Japan | D06M 13/463 |
| 4-41773 | 2/1992 | Japan | D06M 13/325 |
| 4-333667 | 11/1992 | Japan | D06M 13/463 |
| WO89/11522 | 11/1989 | WIPO | C11D 1/62 |
| WO91/01295 | 2/1991 | WIPO | C07C 219/06 |
| 91/17974 | 11/1991 | WIPO | C07C 219/08 |
| 93/17085 | 9/1993 | WIPO | C11D 1/62 |
| 93/21291 | 10/1993 | WIPO | C11D 1/62 |
| 94/10285 | 5/1994 | WIPO | C11D 3/40 |

OTHER PUBLICATIONS

Chemical Abstracts, vol. 118, No. 257026, abstract of JP-4, 333,667 (Nov. 20, 1992).

Application Ser. No. 7,865,596 Inventor Van Phan et al. Filing Date 04/00/92.

Application Ser. No. 07/865,597 Inventor Van Phan et al. Filing Date 04/00/92.

Application Ser. No. 8,004,334 Inventor Van Phan et al. Filing Date 01/00/93.

Application Ser. No. 8,004,333 Inventor Van Phan et al. Filind Date 01/00/1993.

*Primary Examiner*—Gary Geist
*Assistant Examiner*—Deborah D. Carr
*Attorney, Agent, or Firm*—Robert B. Aylor

[57] ABSTRACT

The present invention relates to softening compounds; stable, homogeneous, preferably concentrated, aqueous liquid and solid textile treatment compositions; and intermediate compositions and/or processes for making said compositions.

The compositions of the present invention contain diester quaternary ammonium compounds wherein the fatty acyl groups have an Iodine Value of from greater than about 5 to less than about 100, a cis/trans isomer weight ratio of greater than about 30/70 when the Iodine Value is less than about 25, the level of unsaturation being less than about 65% by weight, wherein said compounds are capable of forming concentrated aqueous compositions with concentrations greater than about 13% by weight at an Iodine Value of greater than about 10 without viscosity modifiers other than normal polar organic solvents present in the raw material of the compound or added electrolyte.

24 Claims, No Drawings

CONCENTRATED BIODEGRADABLE QUATERNARY AMMONIUM FABRIC SOFTENER COMPOSITIONS AND COMPOUDS CONTAINING INTERMEDIATE IODINE VALUE UNSATURATED FATTY ACID CHAINS

CROSS-REFERENCE TO RELATED APPLICATION

This a division of application Ser. No. 08/142,739, filed on Oct. 25, 1993, now abandoned, which is a continuation-in-part of our U.S. patent application Ser. No. 08/024,541, filed Mar. 1, 1993, now abandoned having the same title.

TECHNICAL FIELD

The present invention relates to softening compounds; stable, homogeneous, preferably concentrated, aqueous liquid and solid textile treatment compositions; and intermediate compositions and/or processes for making said compositions. In particular, it especially relates to textile softening compounds and compositions for use in the rinse cycle of a textile laundering operation to provide excellent fabric softening/static control benefits, the compositions being characterized by excellent storage and viscosity stability, as well as biodegradability.

BACKGROUND OF THE INVENTION

The art discloses many problems associated with formulating and preparing stable fabric conditioning formulations. See, for example, U.S. Pat. No. 3,904,533, Nejditch et al. issued Sep. 9, 1975. Japanese Laid Open Publication 1,249, 129, filed Oct. 4, 1989, discloses a problem with dispersing fabric softener actives containing two long hydrophobic chains interrupted by ester linkages ("diester quaternary ammonium compounds") and solves it by rapid mixing. U.S. Pat. No. 5,066,414, Chang, issued Nov. 19, 1991, teaches and claims compositions containing mixtures of quaternary ammonium salts containing at least one ester linkage, nonionic surfactant such as a linear alkoxylated alcohol, and liquid carrier for improved stability and dispersibility. U.S. Pat. No. 4,767,547, Straathof et al., issued Aug. 30, 1988, claims compositions containing either diester, or monoester quaternary ammonium compounds where the nitrogen has either one, two, or three methyl groups, stabilized by maintaining a critical low pH of from 2.5 to 4.2.

U.S. Pat. No. 4,401,578, Verbruggen, issued Aug. 30, 1983 discloses hydrocarbons, fatty acids, fatty acid esters, and fatty alcohols as viscosity control agents for fabric softeners (the fabric softeners are disclosed as optionally comprising ester linkages in the hydrophobic chains). WO 89/115 22-A (DE 3,818,061-A; EP-346,634-A), with a priority of May 27, 1988, discloses diester quaternary ammonium fabric softener components plus a fatty acid. European Pat. No. 243,735 discloses sorbitan esters plus diester quaternary ammonium compounds to improve dispersions of concentrated softener compositions.

Diester quaternary ammonium compounds with a fatty acid, alkyl sulfate, or alkyl sulfonate anion are disclosed in European Pat. No. 336,267-A with a priority of Apr. 2, 1988. U.S. Pat. No. 4,808,321, Walley, issued Feb. 28, 1989, teaches fabric softener compositions comprising monoester analogs of ditallow dimethyl ammonium chloride which are dispersed in a liquid carrier as sub-micron particles through high shear mixing, or particles can optionally be stabilized with emulsifiers such as nonionic $C_{14-18}$ ethoxylates.

E.P. Appln. 243,735, Nusslein et al., published Nov. 4, 1987, discloses sorbitan ester plus diester quaternary ammonium compounds to improve dispersibility of concentrated dispersions.

E.P. Appln. 409,502, Tandela et al., published Jan. 23, 1991, discloses, e.g., ester quaternary ammonium compounds, and a fatty acid material or its salt.

E.P. Appln. 240,727, Nusslein et al., priority date of Mar. 12, 1986, teaches diester quaternary ammonium compounds with soaps or fatty acids for improved dispersibility in water.

The art also teaches compounds that alter the structure of diester quaternary ammonium compounds by substituting, e.g., a hydroxy ethyl for a methyl group or a polyalkoxy group for the alkoxy group in the two hydrophobic chains. Specifically, U.S. Pat. No. 3,915,867, Kang et al., issued Oct. 28, 1975, discloses the substitution of a hydroxyethyl group for a methyl group. A softener material with specific cis/trans content in the long hydrophobic groups is disclosed in Jap. Pat. Appln. 63-194316, filed Nov. 21, 1988. Jap. Pat. Appln. 4-333,667, published Nov. 20, 1992, teaches liquid softener compositions containing diester quaternary ammonium compounds having a total saturated:unsaturated ratio in the ester alkyl groups of 2:98 to 30:70.

All of the above patents and patent applications are incorporated herein by reference.

SUMMARY OF THE INVENTION

The present invention provides biodegradable textile softening compositions and compounds with excellent concentratability, static control, softening, and storage stability of concentrated aqueous compositions. In addition, these compositions provide these benefits under worldwide laundering conditions and minimize the use of extraneous ingredients for stability and static control to decrease environmental chemical load.

The compounds of the present invention are quaternary ammonium compounds wherein the fatty acyl groups have an IV of from greater than about 5 to less than about 100, a cis/trans isomer weight ratio of greater than about 30/70 when the IV is less than about 25, the level of unsaturation being less than about 65% by weight, wherein said compounds are capable of forming concentrated aqueous compositions with concentrations greater than about 13% by weight at an IV of greater than about 10 without viscosity modifiers other than normal polar organic solvents present in the raw material of the compound or added electrolyte, and wherein any fatty acyl groups from tallow must be modified.

The compositions can be aqueous liquids, preferably concentrated, containing from about 5% to about 50%, preferably from about 15% to about 40%, more preferably from about 15% to about 35%, and even more preferably from about 15% to about 32%, of said biodegradable, preferably diester, softening compound, or can be further concentrated to particulate solids, containing from about 50% to about 95%, preferably from about 60% to about 90%, of said softening compound.

Water can be added to the particulate solid compositions to form dilute or concentrated liquid softener compositions with a concentration of said softening compound of from about 5% to about 50%, preferably from about 5% to about 35%, more preferably from about 5% to about 32%. The particulate solid composition can also be used directly in the rinse bath to provide adequate usage concentration (e.g., from about 10 to about 1,000 ppm, preferably from about 50 to about 500 ppm, of total active ingredient). The liquid compositions can be added to the rinse to provide the same usage concentrations. Providing the composition in solid form provides cost savings on shipping the product (less weight) and cost savings on processing the composition (less shear and heat input needed to process the solid form).

The present invention also provides a process for preparation of concentrated aqueous biodegradable textile softener compositions (dispersions) with excellent de-watering of the softener vesicles in said dispersions, involving a two-stage addition of electrolyte which results in more water in the continuous phase and greater fluidity of said concentrated aqueous compositions. This process also involves the addition of perfume at lower than conventional temperatures which retards partitioning of certain perfume components into the softener vesicles, and thereby promotes viscosity stability. In addition, adding perfume to concentrated liquid fabric softeners, at ambient temperature, in a separate mixing vessel minimizes their volatilization and cross-contamination between batches and simplifies the manufacturing operation.

DETAILED DESCRIPTION OF THE INVENTION

(A) Diester Quaternary Ammonium Compound (DEQA)

The present invention relates to DEQA compounds and compositions containing DEQA as an essential component: DEQA having the formula:

$$(R)_{4-m}—N^{+}—[(CH_2)_n—Y—R^2]_m\ X^-$$

wherein each Y=—O—(O)C—, or —C(O)—O—;

m=2 or 3;

each n=1 to 4;

each R substituent is a short chain $C_1$–$C_6$, preferably $C_1$–$C_3$, alkyl group, e.g., methyl (most preferred), ethyl, propyl, and the like, benzyl or mixtures thereof;

each $R^2$ is a long chain, at least partially unsaturated (IV of greater than about 5 to less than about 100), $C_{11}$–$C_{21}$ hydrocarbyl, or substituted hydrocarbyl substituent and the counterion, $X^-$, can be any softener-compatible anion, for example, chloride, bromide, methylsulfate, formate, sulfate, nitrate and the like.

DEQA compounds prepared with fully saturated acyl groups are rapidly biodegradable and excellent softeners. However, it has now been discovered that compounds prepared with at least partially unsaturated acyl groups have many advantages (i.e., concentratability and good storage viscosity) and are highly acceptable for consumer products when certain conditions are met.

Variables that must be adjusted to obtain the benefits of using unsaturated acyl groups include the Iodine Value (IV) of the fatty acids; the cis/trans isomer weight ratios in the fatty acyl groups; and the odor of fatty acid and/or the DEQA. Any reference to IV values hereinafter refers to IV (Iodine Value) of fatty acyl groups and not to the resulting DEQA compound.

When the IV of the fatty acyl groups is above about 20, the DEQA provides excellent antistatic effect. Antistatic effects are especially important where the fabrics are dried in a tumble dryer, and/or where synthetic materials which generate static are used. Maximum static control occurs with an IV of greater than about 20, preferably greater than about 40. When fully saturated DEQA compositions are used, poor static control results. Also, as discussed hereinafter, concentratability increases as IV increases. The benefits of concentratability include: use of less packaging material; use of less organic solvents, especially volatile organic solvents; use of less concentration aids which may add nothing to performance; etc.

As the IV is raised, there is a potential for odor problems. Surprisingly, some highly desirable, readily available sources of fatty acids such as tallow, possess odors that remain with the compound DEQA despite the chemical and mechanical processing steps which convert the raw tallow to finished DEQA. Such sources must be deodorized, e.g., by absorption, distillation (including stripping such as steam stripping), etc., as is well known in the art. In addition, care must be taken to minimize contact of the resulting fatty acyl groups to oxygen and/or bacteria by adding antioxidants, antibacterial agents, etc. The additional expense and effort associated with the unsaturated fatty acyl groups is justified by the superior concentratability and/or performance which was not heretofore recognized. For example, DEQA containing unsaturated fatty acyl groups can be concentrated above about 13% without the need for additional concentration aids, especially surfactant concentration aids as discussed hereinafter.

DEQA derived from highly unsaturated fatty acyl groups, i.e., fatty acyl groups having a total unsaturation above about 65% by weight, do not provide any additional improvement in antistatic effectiveness. They may, however, able to provide other benefits such as improved water absorbency of the fabrics. In general, an IV range of from about 40 to about 65 is preferred for concentratability, maximization of fatty acyl sources, excellent softness, static control, etc.

Highly concentrated aqueous dispersions of these diester compounds can gel and/or thicken during low (40° F.) temperature storage. Diester compounds made from only unsaturated fatty acids minimizes this problem but additionally is more likely to cause malodor formation. Surprisingly, compositions from these diester compounds made from fatty acids having an IV of from about 5 to about 25, preferably from about 10 to about 25, more preferably from about 15 to about 20, and a cis/trans isomer weight ratio of from greater than about 30/70, preferably greater than about 50/50, more preferably greater than about 70/30, are storage stable at low temperature with minimal odor formation. These cis/trans isomer weight ratios provide optimal concentratability at these IV ranges. In the IV range above about 25, the ratio of cis to trans isomers is less important unless higher concentrations are needed. The relationship between IV and concentratability is described hereinafter. For any IV, the concentration that will be stable in an aqueous composition will depend on the criteria for stability (e.g., stable down to about 5° C.; stable down to 0° C.; doesn't gel; gels but recovers on heating, etc.) and the other ingredients present, but the concentration that is stable can be raised by adding the concentration aids, described hereinafter in more detail, to achieve the desired stability.

Generally, hydrogenation of fatty acids to reduce polyunsaturation and to lower IV to insure good color and improve odor and odor stability leads to a high degree of trans configuration in the molecule. Therefore, diester compounds derived from fatty acyl groups having low IV values can be made by mixing fully hydrogenated fatty acid with touch hydrogenated fatty acid at a ratio which provides an IV of from about 5 to about 25. The polyunsaturation content of the touch hardened fatty acid should be less than about 5%, preferably less than about 1%. During touch hardening the cis/trans isomer weight ratios are controlled by methods known in the art such as by optimal mixing, using specific catalysts, providing high $H_2$ availability, etc. Touch hardened fatty acid with high cis/trans isomer weight ratios is available commercially (i.e., Radiacid 406 from FINA).

It has also been found that for good chemical stability of the diester quaternary compound in molten storage, moisture level in the raw material must be controlled and minimized preferably less than about 1% and more preferably less than about 0.5% water. Storage temperatures should be kept low as possible and still maintain a fluid material, ideally in the range of from about 120° F. to about 150° F. The optimum storage temperature for stability and fluidity depends on the specific IV of the fatty acid used to make the diester quaternary and the level/type of solvent selected. It is important to provide good molten storage stability to provide a commercially feasible raw material that will not degrade noticeably in the normal transportation/storage/handling of the material in manufacturing operations.

Compositions of the present invention contain the following levels of DEQA:

I. for solid compositions: from about 50% to about 95%, preferably from about 60% to about 90%, and II. for liquid compositions: from about 5% to about 50%, preferably from about 15% to about 40%, more preferably from about 15% to about 35%, and even more preferably from about 15% to about 32%.

It will be understood that substituents R and $R^2$ can optionally be substituted with various groups such as alkoxyl or hydroxyl groups. The preferred compounds can be considered to be diester variations of ditallow dimethyl ammonium chloride (DTDMAC), which is a widely used fabric softener. At least 80% of the DEQA is in the diester form, and from 0% to about 20%, preferably less than about 10%, more preferably less than about 5%, can be DEQA monoester (e.g., only one —Y—$R^2$ group).

As used herein, when the diester is specified, it will include the monoester that is normally present. For softening, under no/low detergent carry-over laundry conditions the percentage of monoester should be as low as possible, preferably no more than about 2.5%. However, under high detergent carry-over conditions, some monoester is preferred. The overall ratios of diester to monoester are from about 100:1 to about 2:1, preferably from about 50:1 to about 5:1, more preferably from about 13:1 to about 8:1. Under high detergent carry-over conditions, the di/monoester ratio is preferably about 11:1. The level of monoester present can be controlled in the manufacturing of the DEQA.

DEQA compounds prepared with saturated acyl groups, i.e., having an IV of about 5 or less, can be partially substituted for the DEQA compounds of the present invention prepared with unsaturated acyl groups having an IV of greater than about 20. This partial substitution can decrease the odor associated with unsaturated DEQA. The ratio is from about 0.2:1 to about 8:1, preferably from about 0.25:1 to about 4:1, most preferably from about 0.3:1 to about 1.5:1.

The following are non-limiting examples (wherein all longchain alkyl substituents are straight-chain):

Saturated $[HO—CH(CH_3)CH_2][CH_3]+N[CH_2CH_2OC(O)C_{15}H_{31}]_2$ $Br^-$ $[C_2H_5]_2N[CH_2CH_2OC(O)C_{17}H_{35}]_2$ $Cl^-$ $[CH_3][C_2H_5]^+N[CH_2CH_2OC(O)C_{13}H_{27}]_2$ $I^-$ $[C_3H_7][C_2H_5]^+N[CH_2CH_2OC(O)C_{15}H_{31}]_2$ $SO_{4CH_3}$

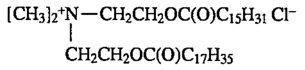

$[CH_3]_2{}^+N[CH_2CH_2OC(O)R^2]_2$ $Cl^-$ where —C(O)$R^2$ is derived from saturated tallow.

Unsaturated $[HO—CH(CH_3)CH_2][CH_3]^+N[CH_2CH_2OC(O)C_{15}H_{29}]_2$ $Br^-$ $[C_2H_5]_2{}^+N[CH_2CH_2OC(O)C_{17}H_{33}]_2$ $Cl^-$ $[CH_3][C_2H_5]^+N[CH_2CH_2OC(O)C_{13}H_{25}]_2$ $I^-$ $[C_3H_7][C_2H_5]^+N[CH_2CH_2OC(O)C_{15}H_{24}]_2$ $SO_4{}^-CH_3$

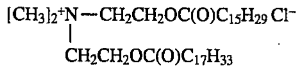

$[CH_2CH_2OH][CH_3]^+N[CH_2CH_2OC(O)R^2]_2$ $Cl^-$ $[CH_3]_2{}^+N[CH_2CH_2OC(O)R^2]_2$ $Cl^-$ where —C(O)$R^2$ is derived from partially hydrogenated tallow or modified tallow having the characteristics set forth herein.

It is especially surprising that careful pH control can noticeably improve product odor stability of compositions using unsaturated DEQA.

In addition, since the foregoing compounds (diesters) are somewhat labile to hydrolysis, they should be handled rather carefully when used to formulate the compositions herein. For example, stable liquid compositions herein are formulated at a pH in the range of from about 2 to about 5, preferably from about 2 to about 4.5, more preferably from about 2 to about 4. For best product odor stability, when the IV is greater that about 25, the pH is from about 2.8 to about 3.5, especially for "unscented" (no perfume) or lightly scented products. This appears to be true for all DEQAs, but is especially true for the preferred DEQA specified herein, i.e., having an IV of greater than about 20, preferably greater than about 40. The limitation is more important as IV increases. The pH can be adjusted by the addition of a Bronsted acid. The pH ranges above are determined without prior dilution of the composition with water.

Examples of suitable Bronsted acids include the inorganic mineral acids, carboxylic acids, in particular the low molecular weight ($C_1$–$C_5$) carboxylic acids, and alkylsulfonic acids. Suitable inorganic acids include HCl, $H_2SO_4$, $HNO_3$ and $H_3PO_4$. Suitable organic acids include formic, acetic, methylsulfonic and ethylsulfonic acid. Preferred acids are hydrochloric, phosphoric, and citric acids.

Synthesis of a Diester Quaternary Ammonium Compound

Synthesis of a preferred biodegradable, diester quaternary ammonium softening compound used herein can be accomplished by the following two-step process:

Step A. Synthesis of Amine

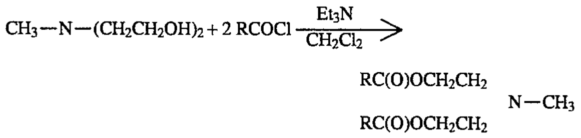

RC(O)=Derived from Deodorized Soft Tallow (touch hardened)

Amine

N-Methyldiethanolamine (440.9 g, 3.69 mol) and triethylamine (561.2 g, 5.54 mol) are dissolved in $CH_2Cl_2$ (12 L) in a 22 L 3-necked flask equipped with an addition funnel, thermometer, mechanical stirrer, condenser, and an argon sweep. Deodorized, touch hardened, soft tallow fatty acid chloride (2.13 kg, 7.39 mol) is dissolved in 2 L $CH_2Cl_2$ and added slowly to the amine solution. The amine solution is then heated to 35° C. to keep the talloyl chloride in solution as it is added. The addition of the acid chloride increased the reaction temperature to reflux (40° C.). The acid chloride addition is slow enough to maintain reflux but not so fast as to lose methylene chloride out of the top of the condenser. The addition should take place over 1.5 hours. The solution is heated at reflux an additional 3 hours. The heat is removed and the reaction stirred 2 hours to cool to room temperature. $CHCl_3$ (12 L) is added. This solution is washed with 1 gallon of saturated NaCl and 1 gallon of saturated $Ca(OH)_2$. The organic layer is allowed to set overnight at room temperature. It is then extracted three times with 50% $K_2CO_3$ (2 gal. each). This is followed by 2 saturated NaCl washes (2 gal. each). Any emulsion that formed during these extractions is resolved by addition of $CHCl_3$ and/or saturated salt and heating on a steam bath. The organic layer is then dried with $MgSO_4$, filtered and concentrated down. Yield is 2.266 kg of soft tallow precursor amine diester. TLC silica (75% $Et_2O$/25% hexane one spot at Rf 0.69).

Step B. Quaternization $$\text{Amine diester} + CH_3Cl \xrightarrow{CH_3CN} (CH)_2N^+(CH_2CH_2O(O)CR)_2\ Cl^-$$

Soft tallow precursor amine (2.166 kg, 3.47 mol) is heated on a steam bath with $CH_3CN$ (1 gal.) until it becomes fluid. The mixture is then poured into a 10 gal., glass-lined, stirred Pfaudler reactor containing $CH_3CN$ (4 gal.). $CH_3Cl$ (25 lbs., liquid) was added via a tube and the reaction is heated to 80° C. for 6 hours. The $CH_3CN$/amine solution is removed from the reactor, filtered and the solid allowed to dry at room temperature over the weekend. The filtrate is roto-evaporated down, allowed to air dry overnight and combined with the other solid. Yield: 2.125 kg white powder.

Diester quaternary ammonium softening compounds can also be synthesized by other processes:

$$(CH_3)-N-(CH_2CH_2OH)_2 + 2ClC(O)C_{15}H_{29} \xrightarrow{(C_2H_5)_3N} CH_3-N-[CH_2CH_2OC(O)C_{15}H_{29}]_2$$

0.6 mole of diethanoL methyl amine is placed in a 3-liter, 3-necked flask equipped with a reflux condenser, argon (or nitrogen) inlet and two addition funnels. In one addition funnel is placed 0.4 moles of triethylamine and in the second addition funnel is placed 1.2 moles of palmitoyl chloride in a 1:1 solution with methylene chloride. Methylene chloride (750 mL) is added to the reaction flask containing the amine and heated to 35° C. (water bath). The triethylamine is added dropwise, and the temperature is raised to 40°–45° C. while stirring over one-half hour. The palmitoyl chloride/methylene chloride solution is added dropwise and allowed to heat at 40°–45° C. under inert atmosphere overnight (12–16 h).

The reaction mixture is cooled to room temperature and diluted with chloroform (1500 mL). The chloroform solution of product is placed in a separatory funnel (4 L) and washed with saturated NaCl, diluted $Ca(OH)_2$, 50% $K_2CO_3$ (3 times)*, and, finally, saturated NaCl. The organic layer is collected and dried over $MgSO_4$, filtered and solvents are removed via rotary evaporation. Final drying is done under high vacuum (0.25 mm Hg).

*Note:

The 50% $K_2CO_3$ layer will be below the chloroform layer.

Step B. Quaternization $$CH_3-N-[CH_2CH_2OC(O)C_{15}H_{29}]_2 \xrightarrow{CH_3Cl} (CH_3)_2-N^+-[CH_2CH_2OC(O)C_{15}H_{29}]_2\ Cl^-$$

0.5 moles of the methyl diethanol palmitoleate amine from Step A is placed in an autoclave sleeve along with 200–300 mL of acetonitrile (anhydrous). The sample is then inserted into the autoclave and purged three times with $N_2$ (16275 mm Hg/21.4 ATM) and once with $CH_3Cl$. The reaction is heated to 80° C. under a pressure of 3604 mm Hg/4.7 ATM in $CH_3Cl$ for 24 hours. The autoclave sleeve is then removed from the reaction mixture. The sample is dissolved in chloroform and solvent is removed by rotary evaporation, followed by drying on high vacuum (0.25 mm Hg).

Another process by which the preferred diester quaternary compound can be made commercially is the reaction of fatty acids (e.g., tallow fatty acids) with methyl diethanolamine. Well known reaction methods are used to form the amine diester precursor. The diester quaternary is then formed by reaction with methyl chloride as previously discussed.

The above reaction processes are generally known in the art for the production of diester softening compounds. To achieve the IV, cis/trans ratios, and percentage unsaturation outlined above, usually additional modifications to these processes must be made.

(B) Optional Viscosity/Dispersibility Modifiers

As stated before, relatively concentrated compositions of the unsaturated DEQA can be prepared that are stable without the addition of concentration aids. However, the compositions of the present invention require organic and/or inorganic concentration aids to go to even higher concentrations and/or to meet higher stability standards depending on the other ingredients. These concentration aids which typically can be viscosity modifiers may be needed, or preferred, for ensuring stability under extreme conditions when particular softener active levels in relation to IV are present.

This relationship between IV and the concentration where concentration aids are needed in a typical aqueous liquid fabric softener composition containing perfume can be defined, at least approximately, by the following equation (for IVs of from greater than about 25 to less than about 100): Concentration of Softener Active (Wt. %)=4.85+0.838 (IV)–0.00756 $(IV)^2$ (where $R^2$=0.99). Above these softener active levels, concentration aids are needed. These numbers are only approximations and if other variables of the formulation change, such as solvent, other ingredients, fatty acids, etc., concentration aids may be required for slightly lower concentrations or not required for slightly higher concentrations. For non-perfume or low level perfume compositions ("unscented" compositions), higher concentrations are possible at given IV levels. If the formulation separates, concentration aids can be added to achieve the desired criteria.

I. Surfactant Concentration Aids

The surfactant concentration aids are typically selected from the group consisting of (1) single long chain alkyl cationic surfactants; (2) nonionic surfactants; (3) amine oxides; (4) fatty acids; or (5) mixtures thereof. The levels of these aids are described below.

(1) The Single-Long-Chain Alkyl Cationic Surfactant

The mono-long-chain-alkyl (water-soluble) cationic surfactants:

I. in solid compositions are at a level of from 0% to about 15%, preferably from about 3% to about 15%, more preferably from about 5% to about 15%, and II. in liquid compositions are at a level of from 0% to about 15%, preferably from about 0.5% to about 10%, the total single-long-chain cationic surfactant being at least at an effective level.

Such mono-long-chain-alkyl cationic surfactants useful in the present invention are, preferably, quaternary ammonium salts of the general formula:

$$[R^2N^+R_3]X^-$$

wherein the $R^2$ group is $C_{10}$–$C_{22}$ hydrocarbon group, preferably $C_{12}$–$C_{18}$ alkyl group or the corresponding ester linkage interrupted group with a short alkylene ($C_1$–$C_4$) group between the ester linkage and the N, and having a similar hydrocarbon group, e.g., a fatty acid ester of choline, preferably $C_{12}$–$C_{14}$ (coco) choline ester and/or $C_{16}$–$C_{18}$ tallow choline ester at from about 0.1% to about 20% by weight of the softener active. Each R is a $C_1$–$C_4$ alkyl or substituted (e.g., hydroxy) alkyl, or hydrogen, preferably methyl, and the counterion $X^-$ is a softener compatible anion, for example, chloride, bromide, methyl sulfate, etc.

The ranges above represent the amount of the single-long-chain-alkyl cationic surfactant which is added to the composition of the present invention. The ranges do not include the amount of monoester which is already present in component (A), the diester quaternary ammonium compound, the total present being at least at an effective level.

The long chain group $R^2$, of the single-long-chain-alkyl cationic surfactant, typically contains an alkylene group having from about 10 to about 22 carbon atoms, preferably from about 12 to about 16 carbon atoms for solid compositions, and preferably from about 12 to about 18 carbon atoms for liquid compositions. This $R^2$ group can be attached to the cationic nitrogen atom through a group containing one, or more, ester, amide, ether, amine, etc., preferably ester, linking groups which can be desirable for increased hydrophilicity, biodegradability, etc. Such linking groups are preferably within about three carbon atoms of the nitrogen atom. Suitable biodegradable single-long-chain alkyl cationic surfactants containing an ester linkage in the long chain are described in U.S. Pat. No. 4,840,738, Hardy and Walley, issued Jun. 20, 1989, said patent being incorporated herein by reference.

If the corresponding, non-quaternary amines are used, any acid (preferably a mineral or polycarboxylic acid) which is added to keep the ester groups stable will also keep the amine protonated in the compositions and preferably during the rinse so that the amine has a cationic group. The composition is buffered (pH from about 2 to about 5, preferably from about 2 to about 4) to maintain an appropriate, effective charge density in the aqueous liquid concentrate product and upon further dilution e.g., to form a less concentrated product and/or upon addition to the rinse cycle of a laundry process.

It will be understood that the main function of the water-soluble cationic surfactant is to lower the viscosity and/or increase the dispersibility of the diester softener and it is not, therefore, essential that the cationic surfactant itself have substantial softening properties, although this may be the case. Also, surfactants having only a single long alkyl chain, presumably because they have greater solubility in water, can protect the diester softener from interacting with anionic surfactants and/or detergent builders that are carried over into the rinse.

Other cationic materials with ring structures such as alkyl imidazoline, imidazolinium, pyridine, and pyridinium salts having a single $C_{12}$–$C_{30}$ alkyl chain can also be used. Very low pH is required to stabilize, e.g., imidazoline ring structures.

Some alkyl imidazolinium salts useful in the present invention have the general formula:

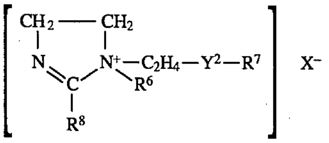

wherein $Y^2$ is —C(O)—O—, —O—(O)—C—, —C(O)—N($R^5$), or —N($R^5$)—C(O)— in which $R^5$ is hydrogen or a $C_1$–$C_4$ alkyl radical; $R^6$ is a $C_1$–$C_4$ alkyl radical; $R^7$ and $R^8$ are each independently selected from R and $R^2$ as defined hereinbefore for the single-long-chain cationic surfactant with only one being $R^2$.

Some alkyl pyridinium salts useful in the present invention have the general formula:

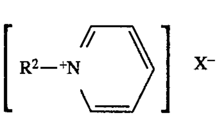

wherein $R^2$ and $X^-$ are as defined above. A typical material of this type is cetyl pyridinium chloride.

(2) Nonionic Surfactant (Alkoxylated Materials)

Suitable nonionic surfactants to serve as the viscosity/dispersibility modifier include addition products of ethylene oxide and, optionally, propylene oxide, with fatty alcohols, fatty acids, fatty amines, etc.

Any of the alkoxylated materials of the particular type described hereinafter can be used as the nonionic surfactant. In general terms, the nonionics herein, when used alone, I. in solid compositions are at a level of from about 5% to about 20%, preferably from about 8% to about 15%, and II. in liquid compositions are at a level of from 0% to about 5%, preferably from about 0.1% to about 5%, more preferably from about 0.2% to about 3%. Suitable compounds are substantially water-soluble surfactants of the general formula:

$$R^2—Y—(C_2H_4O)_z—C_2H_4OH$$

wherein $R^2$ for both solid and liquid compositions is selected from the group consisting of primary, secondary and branched chain alkyl and/or acyl hydrocarbyl groups; primary, secondary and branched chain alkenyl hydrocarbyl groups; and primary, secondary and branched chain alkyl- and alkenyl-substituted phenolic hydrocarbyl groups; said hydrocarbyl groups having a hydrocarbyl chain length of from about 8 to about 20, preferably from about 10 to about 18 carbon atoms. More preferably the hydrocarbyl chain length for liquid compositions is from about 16 to about 18 carbon atoms and for solid compositions from about 10 to about 14 carbon atoms. In the general formula for the ethoxylated nonionic surfactants herein, Y is typically —O—, —C(O)O—, —C(O)N(R)—, or —C(O)N(R)R—, in which $R^2$, and R, when present, have the meanings given hereinbefore, and/or R can be hydrogen, and z is at least about 8, preferably at least about 10–11. Performance and, usually, stability of the softener composition decrease when fewer ethoxylate groups are present.

The nonionic surfactants herein are characterized by an HLB (hydrophilic-lipophilic balance) of from about 7 to about 20, preferably from about 8 to about 15. Of course, by defining $R^2$ and the number of ethoxylate groups, the HLB of the surfactant is, in general, determined. However, it is to be noted that the nonionic ethoxylated surfactants useful herein, for concentrated liquid compositions, contain relatively long chain $R^2$ groups and are relatively highly ethoxylated. While shorter alkyl chain surfactants having short ethoxylated groups may possess the requisite HLB, they are not as effective herein.

Nonionic surfactants as the viscosity/dispersibility modifiers are preferred over the other modifiers disclosed herein for, compositions with higher levels of perfume.

Examples of nonionic surfactants follow. The nonionic surfactants of this invention are not limited to these examples. In the examples, the integer defines the number of ethoxyl (EO) groups in the molecule.

a. Straight-Chain, Primary Alcohol Alkoxylates

The deca-, undeca-, dodeca-, tetradeca-, and pentadeca-ethoxylates of n-hexadecanol, and n-octadecanol having an HLB within the range recited herein are useful viscosity/dispersibility modifiers in the context of this invention. Exemplary ethoxylated primary alcohols useful herein as the viscosity/dispersibility modifiers of the compositions are n-$C_{18}$EO(10); and n-$C_{10}$EO(11). The ethoxylates of mixed natural or synthetic alcohols in the "tallow" chain length range are also useful herein. Specific examples of such materials include tallowalcohol-EO(11), tallowalcohol-EO(18), and tallowalcohol-EO(25).

b. Straight-Chain, Secondary Alcohol Alkoxylates

The deca-, undeca-, dodeca-, tetradeca-, pentadeca-, octadeca-, and nonadeca-ethoxyl ates of 3-hexadecanol, 2-octadecanol, 4-eicosanol, and 5-eicosanol having and HLB within the range recited herein are useful viscosity/dispersibility modifiers in the context of this invention. Exemplary ethoxylated secondary alcohols useful herein as the viscosity/dispersibility modifiers of the compositions are: 2-$C_{16}$EO(11); 2-$C_{20}$EO(11); and 2-$C_{16}$EO(14).

c. Alkyl Phenol Alkoxylates

As in the case of the alcohol alkoxylates, the hexa-through octadeca-ethoxylates of alkylated phenols, particularly monohydric alkylphenols, having an HLB within the range recited herein are useful as the viscosity/dispersibility modifiers of the instant compositions. The hexa- through octadeca-ethoxylates of p-tridecylphenol, m-pentadecylphenol, and the like, are useful herein. Exemplary ethoxylated alkylphenols useful as the viscosity/dispersibility modifiers of the mixtures herein are: p-tridecylphenol EO(11) and p-pentadecylphenol EO(18).

As used herein and as generally recognized in the art, a phenylene group in the nonionic formula is the equivalent of an alkylene group containing from 2 to 4 carbon atoms. For present purposes, nonionics containing a phenylene group are considered to contain an equivalent number of carbon atoms calculated as the sum of the carbon atoms in the alkyl group plus about 3.3 carbon atoms for each phenylene group.

d. Olefinic Alkoxylates

The alkenyl alcohols, both primary and secondary, and alkenyl phenols corresponding to those disclosed immediately hereinabove can be ethoxylated to an HLB within the range recited herein and used as the viscosity/dispersibility modifiers of the instant compositions.

e. Branched Chain Alkoxylates

Branched chain primary and secondary alcohols which are available from the well-known "OXO" process can be ethoxylated and employed as the viscosity/dispersibility modifiers of compositions herein.

The above ethoxylated nonionic surfactants are useful in the present compositions alone or in combination, and the term "nonionic surfactant" encompasses mixed nonionic surface active agents.

(3) Amine Oxides

Suitable amine oxides include those with one alkyl or hydroxyalkyl moiety of about 8 to about 28 carbon atoms, preferably from about 8 to about 16 carbon atoms, and two alkyl moieties selected from the group consisting of alkyl groups and hydroxyalkyl groups with about 1 to about 3 carbon atoms.

The amine oxides:

I. in solid compositions are at a level of from 0% to about 15%, preferably from about 3% to about 15%; and II. in liquid compositions are at a level of from 0% to about 5%, preferably from about 0.25% to about 2%, the total amine oxide present at least at an effective level.

Examples include dimethyloctylamine oxide, diethyldecylamine oxide, bis-(2-hydroxyethyl)dodecylamine oxide, dimethyldodecylamine oxide, dipropyltetradecylamine oxide, methylethylhexadecylamine oxide, dimethyl-2-hydroxyoctadecylamine oxide, and coconut fatty alkyl dimethylamine oxide.

(4) Fatty Acids

Suitable fatty acids include those containing from about 12 to about 25, preferably from about 13 to about 22, more preferably from about 16 to about 20, total carbon atoms, with the fatty moiety containing from about 10 to about 22, preferably from about 10 to about 18, more preferably from about 10 to about 14 (mid cut), carbon atoms. The shorter moiety contains from about 1 to about 4, preferably from about 1 to about 2 carbon atoms.

Fatty acids are present at the levels outlined above for amine oxides. Fatty acids are preferred concentration aids for those compositions which require a concentration aid and contain perfume.

II. Electrolyte Concentration Aids

Inorganic viscosity control agents which can also act like or augment the effect of the surfactant concentration aids, include water-soluble, ionizable salts which can also optionally be incorporated into the compositions of the present invention. A wide variety of ionizable salts can be used. Examples of suitable salts are the halides of the Group IA and I IA metals of the Periodic Table of the Elements, e.g., calcium chloride, magnesium chloride, sodium chloride, potassium bromide, and lithium chloride. The ionizable salts are particularly useful during the process of mixing the ingredients to make the compositions herein, and later to obtain the desired viscosity. The amount of ionizable salts used depends on the amount of active ingredients used in the compositions and can be adjusted according to the desires of the formulator. Typical levels of salts used to control the composition viscosity are from about 20 to about 20,000 parts per million (ppm), preferably from about 20 to about 11,000 ppm, by weight of the composition.

Alkylene polyammonium salts can be incorporated into the composition to give viscosity control in addition to or in place of the water-soluble, ionizable salts above. In addition, these agents can act as scavengers, forming ion pairs with anionic detergent carried over from the main wash, in the rinse, and on the fabrics, and may improve softness performance. These agents may stabilize the viscosity over a broader range of temperature, especially at low temperatures, compared to the inorganic electrolytes.

Specific examples of alkylene polyammonium salts include 1-lysine monohydrochloride and 1,5-diammonium 2-methyl pentane dihydrochloride.

(C) Stabilizers

Stabilizers can be present in the compositions of the present invention. The term "stabilizer," as used herein, includes antioxidants and reductive agents. These agents are present at a level of from 0% to about 2%, preferably from about 0.01% to about 0.2%, more preferably from about 0,035% to about 0.1% for antioxidants, and more preferably from about 0.01% to about 0.2% for reductive agents. These assure good odor stability under long term storage conditions for the compositions and compounds stored in molten form. Use of antioxidants and reductive agent stabilizers is especially critical for unscented or low scent products (no or low perfume).

Examples of antioxidants that can be added to the compositions of this invention include a mixture of ascorbic acid, ascorbic palmitate, propyl gallate, available from Eastman Chemical Products, Inc., under the trade names Tenox® PG and Tenox S-1; a mixture of BHT (butylated hydroxytoluene), BHA (butylated hydroxyanisole), propyl gallate, and citric acid, available from Eastman Chemical Products, Inc., under the trade name Tenox-6; butylated hydroxytoluene, available from UOP Process Division under the trade name Sustane® BHT; tertiary butylhydroquinone, Eastman Chemical Products, Inc., as Tenox TBHQ; natural tocopherols, Eastman Chemical Products, Inc., as Tenox GT-1/GT-2; and butylated hydroxyanisole, Eastman Chemical Products, Inc., as BHA; long chain esters ($C_8$–$C_{22}$)of gallic acid, e.g., dodecyl gallate; Irganox® 1010; Irganox® 1035; Irganox® B 1171; Irganox® 1425; Irganox® 3114; Irganox® 3125; and mixtures thereof; preferably Irganox® 3125, Irganox® 1425, Irganox® 3114, and mixtures thereof; more preferably Irganox® 3125 alone or mixed with citric acid and/or other chelators such as isopropyl citrate, Dequest® 2010, available from Monsanto with a chemical name of 1-hydroxyethylidene-1,1-diphosphonic acid (etidronic acid), and Tiron®, available from Kodak with a chemical name of 4,5-dihydroxy-m-benzene-sulfonic acid/sodium salt, and DTPA®, available from Aldrich with a chemical name of diethylenetriaminepentaacetic acid. The chemical names and CAS numbers for some of the above stabilizers are listed in Table II below.

TABLE II

| Antioxidant | CAS No. | Chemical Name used in Code of Federal Regulations |
|---|---|---|
| Irganox ® 1010 | 6683-19-8 | Tetrakis [methylene(3,5-di-tert-butyl-4 hydroxyhydrocinnamate)] methane |
| Irganox ® 1035 | 41484-35-9 | Thiodiethylene bis(3,5-di-tert-butyl-4-hydroxyhydrocinnamate |
| Irganox ® 1098 | 23128-74-7 | N,N'-Hexamethylene bis(3,5-di-tert-butyl-4-hydroxyhydrocin-nammamide |
| Irganox ® B 1171 | 31570-04-4 23128-74-7 | 1:1 Blend of Irganox ® 1098 and Irgafos ® 168 |
| Irganox ® 1425 | 65140-91-2 | Calcium bis[monoethyl(3,5-di-tert-butyl-4-hydroxybenzyl) phosphonate] |
| Irganox ® 3114 | 27676-62-6 | 1,3,5-Tris(3,5-di-tert-butyl-4-hydroxybenzyl)-s-triazine-2,4,6-(1H, 3H, 5H)trione |

TABLE II-continued

| Antioxidant | CAS No. | Chemical Name used in Code of Federal Regulations |
|---|---|---|
| Irganox ® 3125 | 34137-09-2 | 3,5-Di-tert-butyl-4-hydroxy-hydrocinnamic acid triester with 1,3,5-tris(2-hydroxyethyl)-S-triazine-2,4,6-(1H, 3H, 5H)-trione |
| Irgafos ® 168 | 31570-04-4 | Tris(2,4-di-tert-butyl-phenyl)phosphite |

Examples of reductive agents include sodium borohydride, hypophosphorous acid, Irgafos® 168, and mixtures thereof.

(D) Liquid Carrier

The liquid carrier employed in the instant compositions is preferably at least primarily water due to its low cost relative availability, safety, and environmental compatibility. The level of water in the liquid carrier is at least about 50%, preferably at least about 60%, by weight of the carrier. The level of liquid carrier is less than about 70, preferably less than about 65, more preferably less than about 50. Mixtures of water and low molecular weight, e.g., <100, organic solvent, e.g., lower alcohol such as ethanol, propanol, isopropanol or butanol are useful as the carrier liquid. Low molecular weight alcohols include monohydric, dihydric (glycol, etc.) trihydric (glycerol, etc.), and higher polyhydric (polyols) alcohols.

(E) Optional Ingredients (1) Optional Soil Release Agent

Optionally, the compositions herein contain from 0% to about 10%, preferably from about 0.1% to about 5%, more preferably from about 0.1% to about 2%, of a soil release agent. Preferably, such a soil release agent is a polymer. Polymeric soil release agents useful in the present invention include copolymeric blocks of terephthalate and polyethylene oxide or polypropylene oxide, and the like. U.S. Pat. No. 4,956,447, Gosselink/Hardy/Trinh, issued Sep. 11, 1990, discloses specific preferred soil release agents comprising cationic functionalities, said patent being incorporated herein by reference.

A preferred soil release agent is a copolymer having blocks of terephthalate and polyethylene oxide. More specifically, these polymers are comprised of repeating units of ethylene and/or propylene terephthalate and polyethylene oxide terephthalate at a molar ratio of ethylene terephthalate units to polyethylene oxide terephthalate units of from about 25:75 to about 35:65, said polyethylene oxide terephthalate containing polyethylene oxide blocks having molecular weights of from about 300 to about 2000. The molecular weight of this polymeric soil release agent is in the range of from about 5,000 to about 55,000.

Another preferred polymeric soil release agent is a crystallizable polyester with repeat units of ethylene terephthalate units containing from about 10% to about 15% by weight of ethylene terephthalate units together with from about 10% to about 50% by weight of polyoxyethylene terephthalate units, derived from a polyoxyethylene glycol of average molecular weight of from about 300 to about 6,000, and the molar ratio of ethylene terephthalate units to polyoxyethylene terephthalate units in the crystallizable polymeric compound is between 2:1 and 6:1. Examples of this polymer include the commercially available materials Zelcon® 4780 (from DuPont) and Milease® T ( from ICI).

Highly preferred soil release agents are polymers of the generic formula (I):

$$X-(OCH_2CH_2)_n(O-\overset{\overset{O}{\|}}{C}-R^1-\overset{\overset{O}{\|}}{C}-OR^2)_u(O-\overset{\overset{O}{\|}}{C}-R^1-\overset{\overset{O}{\|}}{C}-O)(CH_2CH_2O)_n-X \quad (I)$$

in which X can be any suitable capping group, with each X being selected from the group consisting of H, and alkyl or acyl groups containing from about 1 to about 4 carbon atoms, preferably methyl. n is selected for water solubility and generally is from about 6 to about 113, preferably from about 20 to about 50. u is critical to formulation in a liquid composition having a relatively high ionic strength. There should be very little material in which u is greater than 10. Furthermore, there should be at least 20% preferably at least 40% of material in which u ranges from about 3 to about 5.

The $R^1$ moieties are essentially 1,4-phenylene moieties. As used herein, the term "the $R^1$ moieties are essentially 1,4-phenylene moieties" refers to compounds where the $R^1$ moieties consist entirely of 1,4-phenylene moieties, or are partially substituted with other arylene or alkarylene moieties, alkylene moieties, alkenylene moieties, or mixtures thereof. Arylene and alkarylene moieties which can be partially substituted for 1,4-phenylene include 1,3-phenylene, 1,2-phenylene, 1,8-naphthylene, 1,4-naphthylene, 2,2-biphenylene, 4,4-biphenylene and mixtures thereof. Alkylene and alkenylene moieties which can be partially substituted include ethylene, 1,2-propylene, 1,4-butylene, 1,5-pentylene, 1,6-hexamethylene, 1,7-heptamethylene, 1,8-octamethylene, 1,4-cyclohexylene, and mixtures thereof.

For the $R^1$ moieties, the degree of partial substitution with moieties other than 1,4-phenylene should be such that the soil release properties of the compound are not adversely affected to any great extent. Generally, the degree of partial substitution which can be tolerated will depend upon the backbone length of the compound, i.e., longer backbones can have greater partial substitution for 1,4-phenylene moieties. Usually, compounds where the $R^1$ comprise from about 50% to about 100% 1,4-phenylene moieties (from 0 to about 50% moieties other than 1,4-phenylene) have adequate soil release activity. For example, polyesters made according to the present invention with a 40:60 mole ratio of isophthalic (1,3-phenylene) to terephthalic (1,4-phenylene) acid have adequate soil release activity. However, because most polyesters used in fiber making comprise ethylene terephthalate units, it is usually desirable to minimize the degree of partial substitution with moieties other than 1,4-phenylene for best soil release activity. Preferably, the $R^1$ moieties consist entirely of (i.e., comprise 100%) 1,4-phenylene moieties, i.e., each $R^1$ moiety is 1,4-phenylene.

For the $R^2$ moieties, suitable ethylene or substituted ethylene moieties include ethylene, 1,2-propylene, 1,2-butylene, 1,2-hexylene, 3-methoxy-1,2-propylene and mixtures thereof. Preferably, the $R^2$ moieties are essentially ethylene moieties, 1,2-propylene moieties or mixture thereof. Inclusion of a greater percentage of ethylene moieties tends to improve the soil release activity of compounds. Inclusion of a greater percentage of 1,2-propylene moieties tends to improve the water solubility of the compounds.

Therefore, the use of 1,2-propylene moieties or a similar branched equivalent is desirable for incorporation of any substantial part of the soil release component in the liquid fabric softener compositions. Preferably, from about 75% to about 100%, more preferably from about 90% to about 100%, of the $R^2$ moieties are 1,2-propylene moieties.

The value for each n is at least about 6, and preferably is at least about 10. The value for each n usually ranges from about 12 to about 113. Typically, the value for each n is in the range of from about 12 to about 43.

A more complete disclosure of these highly preferred soil release agents is contained in European Pat. Application 185,427, Gosselink, published Jun. 25, 1986, incorporated herein by reference.

(2) Optional Bacteriocides

Examples of bacteriocides that can be used in the compositions of this invention are parabens, especially methyl, glutaraldehyde, formaldehyde, 2-bromo-2-nitropropane-1,3-diol sold by Inolex Chemicals under the trade name Bronopol®, and a mixture of 5-chloro-2-methyl-4-isothiazoline-3-one and 2-methyl-4-isothiazoline-3-one sold by Rohm and Haas Company under the trade name Kathon® CG/ICP. Typical levels of bacteriocides used in the present compositions are from about 1 to about 2,000 ppm by weight of the composition, depending on the type of bacteriocide selected. Methyl paraben is especially effective for mold growth in aqueous fabric softening compositions with under 10% by weight of the diester compound.

(3) Other Optional Ingredients

The present invention can include other optional components conventionally used in textile treatment compositions, for example, colorants, perfumes, preservatives, optical brighteners, opacifiers, fabric conditioning agents, surfactants, stabilizers such as guar gum and polyethylene glycol, anti-shrinkage agents, anti-wrinkle agents, fabric crisping agents, spotting agents, germicides, fungicides, anti-corrosion agents, antifoam agents, and the like.

An optional additional softening agent of the present invention is a nonionic fabric softener material. Typically, such nonionic fabric softener materials have an HLB of from about 2 to about 9, more typically from about 3 to about 7. Such nonionic fabric softener materials tend to be readily dispersed either by themselves, or when combined with other materials such as single-long-chain alkyl cationic surfactant described in detail hereinbefore. Dispersibility can be improved by using more single-long-chain alkyl cationic surfactant, mixture with other materials as set forth hereinafter, use of hotter water, and/or more agitation. In general, the materials selected should be relatively crystalline, higher melting, (e.g., >~50° C.) and relatively water-insoluble.

The level of optional nonionic softener in the solid composition is typically from about 10% to about 40%, preferably from about 15% to about 30%, and the ratio of the optional nonionic softener to DEQA is from about 1:6 to about 1:2, preferably from about 1:4 to about 1:2. The level of optional nonionic softener in the liquid composition is typically from about 0.5% to about 10%, preferably from about 1% to about 5%.

Preferred nonionic softeners are fatty acid partial esters of polyhydric alcohols, or anhydrides thereof, wherein the alcohol, or anhydride, contains from 2 to about 18, preferably from 2 to about 8, carbon atoms, and each fatty acid moiety contains from about 12 to about 30, preferably from about 16 to about 20, carbon atoms. Typically, such softeners contain from about one to about 3, preferably about 2 fatty acid groups per molecule.

The polyhydric alcohol portion of the ester can be ethylene glycol, glycerol, poly (e.g., di-, tri-, tetra, penta-, and/or hexa-) glycerol, xylitol, sucrose, erythritol, pentaerythritol, sorbitol or sorbitan. Sorbitan esters and polyglycerol monostearate are particularly preferred.

The fatty acid portion of the ester is normally derived from fatty acids having from about 12 to about 30, preferably from about 16 to about 20, carbon atoms, typical examples of said fatty acids being lauric acid, myristic acid, palmitic acid, stearic acid and behenic acid.

Highly preferred optional nonionic softening agents for use in the present invention are the sorbitan esters, which are esterified dehydration products of sorbitol, and the glycerol esters.

Sorbitol, which is typically prepared by the catalytic hydrogenation of glucose, can be dehydrated in well known fashion to form mixtures of 1,4- and 1,5-sorbitol anhydrides and small amounts of isosorbides. (See U.S. Pat. No. 2,322,821, Brown, issued Jun. 29, 1943, incorporated herein by reference.)

The foregoing types of complex mixtures of anhydrides of sorbitol are collectively referred to herein as "sorbitan." It will be recognized that this "sorbitan" mixture will also contain some free, uncyclized sorbitol.

The preferred sorbitan softening agents of the type employed herein can be prepared by esterifying the "sorbitan" mixture with a fatty acyl group in standard fashion, e.g., by reaction with a fatty acid halide or fatty acid. The esterification reaction can occur at any of the available hydroxyl groups, and various mono-, di-, etc., esters can be prepared. In fact, mixtures of mono-, di-, tri-, etc., esters almost always result from such reactions, and the stoichiometric ratios of the reactants can be simply adjusted to favor the desired reaction product.

For commercial production of the sorbitan ester materials, etherification and esterification are generally accomplished in the same processing step by reacting sorbitol directly with fatty acids. Such a method of sorbitan ester preparation is described more fully in MacDonald; "Emulsifiers:" Processing and Quality Control:, *Journal of the American Oil Chemists' Society*, Vol. 45, October 1968.

Details, including formula, of the preferred sorbitan esters can be found in U.S. Pat. No. 4,128,484, incorporated hereinbefore by reference.

Certain derivatives of the preferred sorbitan esters herein, especially the "lower" ethoxylates thereof (i.e., mono-, di-, and tri-esters wherein one or more of the unesterified —OH groups contain one to about twenty oxyethylene moieties [Tweens®] are also useful in the composition of the present invention. Therefore, for purposes of the present invention, the term "sorbitan ester" includes such derivatives.

For the purposes of the present invention, it is preferred that a significant amount of di- and tri- sorbitan esters are present in the ester mixture. Ester mixtures having from 20–50% mono-ester, 25–50% di-ester and 10–35% of tri- and tetra-esters are preferred.

The material which is sold commercially as sorbitan monoester (e.g., monostearate) does in fact contain significant amounts of di- and tri-esters and a typical analysis of sorbitan monostearate indicates that it comprises about 27% mono-, 32% di- and 30% tri- and tetra-esters. Commercial sorbitan monostearate therefore is a preferred material. Mixtures of sorbitan stearate and sorbitan palmitate having stearate/palmitate weight ratios varying between 10:1 and 1:10, and 1,5-sorbitan esters are useful. Both the 1,4- and 1,5-sorbitan esters are useful herein.

Other useful alkyl sorbitan esters for use in the softening compositions herein include sorbitan monolaurate, sorbitan monomyristate, sorbitan monopalmitate, sorbitan monobehenate, sorbitan monooleate, sorbitan dilaurate, sorbitan dimyristate, sorbitan dipalmitate, sorbitan distearate, sorbitan dibehenate, sorbitan dioleate, and mixtures thereof, and mixed tallowalkyl sorbitan mono- and di-esters. Such mixtures are readily prepared by reacting the foregoing hydroxy-substituted sorbitans, particularly the 1,4- and 1,5-sorbitans, with the corresponding acid or acid chloride in a simple esterification reaction. It is to be recognized, of course, that commercial materials prepared in this manner will comprise mixtures usually containing minor proportions of uncyclized sorbitol, fatty acids, polymers, isosorbide structures, and the like. In the present invention, it is preferred that such impurities are present at as low a level as possible.

The preferred sorbitan esters employed herein can contain up to about 15% by weight of esters of the $C_{20}$–$C_{26}$, and higher, fatty acids, as well as minor amounts of $C_8$, and lower, fatty esters.

Glycerol and polyglycerol esters, especially glycerol, diglycerol, triglycerol, and polyglycerol mono- and/or diesters, preferably mono-, are also preferred herein (e.g., polyglycerol monostearate with a trade name of Radiasurf 7248). Glycerol esters can be prepared from naturally occurring triglycerides by normal extraction, purification and/or interesterification processes or by esterification processes of the type set forth hereinbefore for sorbitan esters. Partial esters of glycerin can also be ethoxylated to form usable derivatives that are included within the term "glycerol esters."

Useful glycerol and polyglycerol esters include monoesters with stearic, oleic, palmitic, lauric, isostearic, myristic, and/or behenic acids and the diesters of stearic, oleic, palmitic, lauric, isostearic, behenic, and/or myristic acids. It is understood that the typical mono-ester contains some di- and tri-ester, etc.

The "glycerol esters" also include the polyglycerol, e.g., diglycerol through octaglycerol esters. The polyglycerol polyols are formed by condensing glycerin or epichlorohydrin together to link the glycerol moieties via ether linkages. The mono- and/or diesters of the polyglycerol polyols are preferred, the fatty acyl groups typically being those described hereinbefore for the sorbitan and glycerol esters.

(F) A Preferred Process for Preparation of Concentrated Aqueous Biodegradable Textile Softener Compositions (Dispersions)

This invention also includes a preferred process for preparing concentrated aqueous biodegradable quaternary ammonium fabric softener compositions/dispersions having ≧28% of biodegradable fabric softener active, including those described in copending U.S. patent application Ser. No. 07/881,979, filed May 12, 1992, Baker et al., said application being incorporated herein by reference. A molten organic premix of the fabric softener active and any other organic materials, but preferably not the perfumes, is dispersed into a water seat at about 104° F. The dispersion is then cooled to about 30° F. to about 60°F. above the major thermal transition temperature of the biodegradable fabric softener active. Electrolyte, as described hereinbefore, is then added in a range of from about 400 ppm to about 7,000 ppm, more preferably from about 1,000 ppm to about 5,000 ppm, most preferably from about 2,000 ppm to about 4,000 ppm, at about 30° F.–60° F. above the major thermal transition temperature. High shear milling is conducted at a temperature of from about 50° F. to about 59° F. above the major thermal transition temperature of the biodegradable fabric softener active. The dispersion is then cooled to ambient temperature and the remaining electrolyte is added, typically in an amount of from about 600 ppm to about 8,000 ppm, more preferably from about 2,000 ppm to about 5,000 ppm, most preferably from about 2,000 ppm to about 4,000 ppm at ambient temperature. As a preferred option, perfume is added at ambient temperature before adding the remaining electrolyte.

The said organic premix is, typically, comprised of said biodegradable fabric softener active and, preferably, at least an effective amount of low molecular weight alcohol processing aid, e.g., ethanol or isopropanol, preferably ethanol.

The above described preferred process provides a convenient method for preparing concentrated aqueous biodegradable fabric softener dispersions, as recited herein, when the biodegradable fabric softening composition consists of from about 28% to about 40%, more preferably from about 28% to about 35%, most preferably from about 28% to about 32%, of total biodegradable fabric softener active, and from about 1,000 ppm to about 15,000 ppm, more preferably from about 3,000 ppm to about 10,000 ppm, most preferably from about 4,000 ppm to about 8,000 ppm, of total electrolyte.

In a preferred process for preparing concentrated aqueous biodegradable fabric softener dispersions as described above, the perfume is added at ambient temperature at a concentration of from about 0.1% to about 2%, preferably from abut 0.5% to about 1.5%, most preferably from about 0.8% to about 1.4%, by weight of the total aqueous dispersion.

In the method aspect of this invention, fabrics or fibers are contacted with an effective amount, generally from about 10 ml to about 150 ml (per 3.5 kg of fiber or fabric being treated) of the softener actives (including diester compound) herein in an aqueous bath. Of course, the amount used is based upon the judgment of the user, depending on concentration of the composition, fiber or fabric type, degree of softness desired, and the like. Preferably, the rinse bath contains from about 10 to about 1,000 ppm, preferably from about 50 to about 500 ppm, of the DEQA fabric softening compounds herein.

The granules can be formed by preparing a melt, solidifying it by cooling, and then grinding and sieving to the desired size. It is highly preferred that the primary particles of the granules have a diameter of from about 50 to about 1,000, preferably from about 50 to about 400, more preferably from about 50 to about 200, microns. The granules can comprise smaller and larger particles, but preferably from about 85% to about 95%, more preferably from about 95% to about 100%, are within the indicated ranges. Smaller and larger particles do not provide optimum emulsions/dispersions when added to water. Other methods of preparing the primary particles can be used including spray cooling of the melt. The primary particles can be agglomerated to form a dust-free, non-tacky, free-flowing powder. The agglomeration can take place in a conventional agglomeration unit (i.e., Zig-Zag Blender, Lodige) by means of a water-soluble binder. Examples of water-soluble binders useful in the above agglomeration process include glycerol, polyethylene glycols, polymers such as PVA, polyacrylates, and natural polymers such as sugars.

The flowability of the granules can be improved by treating the surface of the granules with flow improvers such as clay, silica or zeolite particles, water-soluble inorganic salts, starch, etc.

EXAMPLES I and IA

| Component | I Wt. % | Ia Wt. % |
|---|---|---|
| Diester Compound[1] | 26.0 | 26.0 |
| Hydrochloric Acid | 0.018 | 0.0082 |
| Citric Acid | — | 0.005 |
| Liquitint ® Blue 651 Dye (1%) | 0.25 | 0.25 |
| Perfume | 1.35 | 1.35 |
| Tenox ® S-1 | 0.10 | — |
| Irganox ® 3125 | — | 0.035 |
| Kathon ® (1.5%) | 0.02 | 0.02 |

-continued

| Component | I Wt. % | Ia Wt. % |
|---|---|---|
| DC-2210 Antifoam (10%) | 0.15 | 0.15 |
| $CaCl_2$ Solution (15%) | 4.33 | 3.33 |
| DI Water | Balance | Balance |
| pH = 2.8-3.5 | | |
| Viscosity = 35–60 cps. | | |

[1]Di(soft tallowoyloxyethyl)dimethyl ammonium chloride where the fatty acyl groups are derived from fatty acids with IVs and cis/trans isomer ratios as outlined in Table I. The diester includes monoester at a weight ratio of 11:1 diester to monoester.

The above compositions are made by the following process:

1. Separately, heat the diester compound premix with the Irganox 3125 and the water seat containing HCl, citric acid (if used), and antifoam agent to 165°±5° F.; (Note: for Ia, the citric acid can totally replace HCl, if desired);
2. Add the diester compound premix into the water seat over 5–6 minutes. During the injection, both mix (600–1,000 rpm) and mill (8,000 rpm with an IKA Ultra Turrax T-50 Mill) the batch.
3. Add 500 ppm of $CaCl_2$ at approximately halfway through the injection.
4. Add 2,000 ppm $CaCl_2$ over 2–7 minutes (200–2,500 ppm/minute) with mixing at 800–1,000 rpm after premix injection is complete at about 150°–165° F.
5. Add perfume over 30 seconds at 145°–155° F.
6. Add dye and Kathon and mix for 30–60 seconds. Cool batch to 70°–80° F.
7. Add 2,500 ppm to 4,000 ppm $CaCl_2$ to cooled batch and mix.

The fatty acids in Table I, used to make the diester compounds of Examples I and Ia have the following characteristics. The process of forming the diester compounds is as set forth hereinbefore.

TABLE I

| | 1 | 2 | 3 | 4 |
|---|---|---|---|---|
| Iodine Value | 43.0 | 53.9 | 53.6 | 39.8 |
| % Unsaturation | 45.18 | 45.44 | 42.76 | 36.57 |
| $C_{18}$ Cis/Trans Ratio | 0.56 | 11.22 | 13.00 | 1.41 |
| % Cis | 15.06 | 36.54 | 33.77 | 20.72 |
| % Trans | 26.95 | 3.26 | 2.60 | 14.65 |
| | 5 | 6 | 7 | 8 |
| Iodine Value | 55.0 | 56.7 | 56.3 | 47.4 |
| % Unsaturation | 51.15 | 51.33 | 47.04 | 44.31 |
| $C_{18}$ Cis/Trans Ratio | 9.12 | 13.93 | 12.17 | 6.14 |
| % Cis | 40.30 | 40.33 | 36.73 | 34.14 |
| % Trans | 4.42 | 2.90 | 3.02 | 5.56 |
| | 9 | 10 | | |
| Iodine Value | 55.0 | 40.1 | | |
| % Unsaturation | 51.30 | 35.81 | | |
| $C_{18}$ Cis/Trans Ratio | 12.91 | 2.01 | | |
| % Cis | 40.12 | 22.25 | | |
| % Trans | 3.10 | 11.10 | | |

Examples II–VII are diester compounds derived from the fatty acid of Table I, Number 2, with an IV of 53.9 and were stored in molten form. These examples are relative measures of activity and are not absolute values based on HPLC. Examples II, IV, and VI initially contain 15.9% ethanol and 0.21% water. Examples III, V, and VII initially contain 18.8% isopropyl alcohol and 0.2% water.

EXAMPLE II

| | (120° F./49° C.) | | |
|---|---|---|---|
| | Fresh Wt. % | 1 Wk Wt. % | 3 Wks Wt. % |
| Diester | 69 | 64 | 67 |
| Monoester | 9 | 8 | 9 |

EXAMPLE III

| | (120° F./49° C.) | | |
|---|---|---|---|
| | Fresh Wt. % | 1 Wk Wt. % | 3 Wks Wt. % |
| Diester | 68 | 71 | 67 |
| Monoester | 9 | 9 | 9 |

EXAMPLE IV

| | (150° F./66° C.) | | |
|---|---|---|---|
| | Fresh Wt. % | 1 Wk Wt. % | 3 Wks Wt. % |
| Diester | 69 | 68 | 67 |
| Monoester | 9 | 8 | 9 |

EXAMPLE V

| | (150° F./66° C.) | | |
|---|---|---|---|
| | Fresh Wt. % | 1 Wk Wt. % | 3 Wks Wt. % |
| Diester | 68 | 67 | 68 |
| Monoester | 9 | 9 | 10 |

EXAMPLE VI

| | (180° F./82° C.) | | |
|---|---|---|---|
| | Fresh Wt. % | 1 Wk Wt. % | 3 Wks Wt. % |
| Diester | 69 | 67 | 61 |
| Monoester | 9 | 11 | 15 |

EXAMPLE VII

| | (180° F./82° C.) | | |
|---|---|---|---|
| | Fresh Wt. % | 1 Wk Wt. % | 3 Wks Wt. % |
| Diester | 68 | 65 | 61 |
| Monoester | 9 | 11 | 13 |

No degradation is observed over 3 weeks storage at 120° F./49° C. to 150° F./66° C. About 10% relative degradation is observed over 3 weeks at 180° F./82° C.

EXAMPLE VIII

| | Wt. % | Wt. % | Wt. % | Wt. % |
|---|---|---|---|---|
| Diester Compound[1] | 32 | 32 | 32 | 32 |
| Hydrochloric Acid | — | — | — | 0.10 |
| DC-2210 Antifoam (10%) | 0.10 | 0.10 | 0.10 | 0.10 |
| $CaCl_2$ Solution (15%) | 5.0 | 5.0 | 5.0 | 5.0 |
| Coco Choline Ester | 1.00 | — | — | — |
| Tallow Choline Ester | — | 1.00 | — | — |
| Coco Fatty Acid | — | — | 0.25 | — |
| Coco Dimethyl Amine Oxide | — | — | — | 1.00 |
| DI Water | 61.65 | 61.65 | 62.40 | 61.55 |

[1]Di(soft tallowoyloxyethyl)dimethyl ammonium chloride where the fatty acyl groups are derived from fatty acids with an IV of 55.

The above compositions are made by the following process:

(A) inject the diester compound premix plus fatty acid, having a temperature of from about 130° F. to about 190° F., preferably 140°–160° F., into an acid water seat, plus choline ester or amine oxide (when present) and antifoam (when present), having a temperature of from about 130° F. to about 190° F.; preferably 140°–160° F., under agitation over about 3 minutes.

(B) add about 3,750 ppm of $CaCl_2$ over 5 minutes solution after premix injection is complete and temperature has dropped to 100°–130° F.;

(C) mill composition for about 2 minutes at 7,000 rpm (IKA Ultra Turrax Mill) after $CaCl_2$ addition;

(D) add about 3,750 ppm of $CaCl_2$ solution after the batch is cooled to a temperature of from about 55° F. to about 95° F.

If inclusion of perfume in the composition is desired, the perfume is preferably added either during or after milling step (C), and after the temperature drops to ≦130° F.

EXAMPLE IX

Solid Particulate Compositions Plus Water to Form Liquid Compositions

| Component | 1 Wt. % | 2 Wt. % | 3 Wt. % |
|---|---|---|---|
| Diester Compound[(1)] | 8.1 | 7.74 | 6.00 |
| Ethoxylated Fatty Alcohol[(2)] | 0.5 | 0.86 | — |
| PGMS[(3)] | — | — | 1.74 |
| Coconut Choline Ester Chloride | — | — | 0.86 |
| Minors (Perfume; Antifoam) | 0.35 | 0.35 | 0.35 |
| **Component** | **4 Wt. %** | **5 Wt. %** | **6 Wt. %** |
| Diester Compound[(1)] | 7.6 | 7.6 | 7.6 |
| Ethoxylated Fatty Alcohol[(2)] | 1 | 1 | 1 |
| **Component** | **7 Wt. %** | **8 Wt. %** | **9 Wt. %** |
| Diester Compound[(1)] | 7.6 | 8.1 | 23.5 |
| Ethoxylated Fatty Alcohol[(2)] | 1 | — | — |
| PGMS[(3)] | | | |
| Coconut Choline Ester Chloride | — | 0.5 | 2.5 |
| Minors (Perfume; Antifoam) | — | 0.35 | 1.5 |
| Electrolyte | — | — | 0.4 |

[(1)]Di(soft tallowoyloxyethyl)dimethyl ammonium chloride where the fatty acyl groups are derived from fatty acids with IVs and cis/trans isomer weight ratios as outlined in Table I.
[(2)]1 and 2 are $C_{16}$–$C_{18}$ $E_{18}$; 4 is $C_{16}$–$C_{18}$ $E_{11}$; 5 is $C_{16}$–$C_{18}$ $E_{18}$; 6 is $C_{16}$–$C_{18}$ $E_{50}$; and 7 is $C_{10}$ $E_{11}$.
[(3)]Polyglycerol monostearate having a trade name of Radiasurf 7248.

The above liquid compositions are made from the corresponding solid compositions having the same active material, on a 100% active weight basis, by the procedure given below. This shows the surprising ability of the solid particulate compositions herein to effectively disperse following simple addition to lukewarm water with gentle agitation (e.g., manual shaking). Improved results are obtained by using higher temperatures and/or effective mixing conditions, e.g., high shear mixing, milling, etc. However, even the mild conditions provide acceptable aqueous compositions.

Procedure

Molten diester is mixed with molten ethoxylated fatty alcohol or molten coconut choline ester chloride. In No. 3, molten PGMS is also added. The mixture is cooled and solidified by pouring onto a metal plate, and then ground. The solvent is removed by a Rotovapor® (2 hrs. at 40°–50° C. at maximum vacuum). The resulting powder is ground and sieved. The reconstitution of the powder is standardized as follows:

The total active solid is 8.6% (diester plus ethoxylated fatty alcohol). Tap water is heated to 35° C. (95° F.). Antifoam is added to the water. The active powder is mixed with the perfume powder. This mix is sprinkled on the water under continuous agitation (up to 2,000 rpm for 10 minutes). This product is cooled by means of a cooling spiral prior to storage. The fresh product is transferred to a bottle and left standing to cool.

EXAMPLE X

Viscosity Stability of Compositions Containing Diester Compound

| Component | A Wt. % | B Wt. % |
|---|---|---|
| Diester Compound(1) | 20 | 20 |
| $CaCl_2$ | 0.072 | 0.072 |
| HCl | 0.07 | 0.07 |
| DI Water | Balance | Balance |

(1)A is a hard di(tallowoyloxyethyl)dimethyl ammonium chloride with a fatty acid IV of <3, virtually all unsaturation being in the trans form. B is partly unsaturated di(alkyloxyethyl) dimethyl ammonium chloride with the following approximate distribution: $C_{14}$ (4%), $C_{16}$ (30%), $C_{18}$ (65%). The fatty acid IV is 11.3, containing 12.6% of $C_{18}$ single unsaturate. This $C_{18}$ unsaturate contains 70% (8.87% total alkyl) cis isomer and 30% trans isomer (3.8% total alkyl).

| | | Viscosity (m Pas) | | | |
|---|---|---|---|---|---|
| | | 4° C. | 10° C. | Ambient | 35° C. |
| A: | Fresh | — | — | 30 | — |
| | 3 days | 680 | 28 | 25 | 30 |
| | 1 week | Gel | 800 | 20 | 32 |
| | 2 weeks | Gel | Gel | 15 | 48 |
| B: | Fresh | — | — | 27 | — |
| | 3 days | 35 | 32 | 25 | 32 |
| | 1 week | 40 | 34 | 25 | 27 |
| | 2 weeks | 52 | 35 | 27 | 30 |

EXAMPLE XI

Concentrated Diester Compositions with Low Temperature Stability

| Component | Wt. % |
|---|---|
| Diester Compound(1) | 22.7 |
| PGMS(2) | 3.5 |
| Tallow alcohol ethoxylate (25) | 1.5 |
| Soil Release Polymer(3) | 0.33 |
| Silicone Antifoam | 0.019 |
| $CaCl_2$ | 0.29 |
| HCl | 0.08 |
| PEG 4000 | 0.60 |
| Minors | 1.00 |
| DI Water | Balance |

(1)Soft di(tallowoyloxyethyl)dimethyl ammonium chloride where the fatty acyl group is derived from fatty acids with an IV of 18 and a cis/trans isomer weight ratio of 70/30.
(2)Polyglycerol monostearate having a trade name of Radiasurf 248.
(3)Copolymer of ethylene oxide and terephthalate with the generic soil release formula (I) wherein each X is methyl, each n is 40, u is 4, each $R^1$ is essentially 1,4-phenylene moieties, each $R^2$ is essentially ethylene, 1,2-propylene moieties, or mixtures thereof.

EXAMPLE XII

Stable Molten Diester Compounds

| Component | A Wt. % | B Wt. % | C Wt. % | D Wt. % |
|---|---|---|---|---|
| Diester Compound(1) | 77.0 | 76.0 | 76.5 | 77.0 |
| Monoester Compound | 4.0 | 6.1 | 7.0 | 7.0 |
| Diesteramine and Diesteramine HCl | 3.2 | 3.0 | 2.4 | 2.5 |
| Fatty Acid | 1.5 | 0.5 | 0.5 | 0.3 |
| Isopropyl Alcohol | 14.0 | 14.0 | — | — |
| Ethanol | — | — | 13.1 | 13.6 |
| Water | 0.1 | 0.2 | 0.4 | 0.1 |
| BHT | 0.1 | 0.1 | — | — |
| Propyl Gallate | — | — | 0.1 | — |
| Irganox ® 3125 | — | — | — | 0.05 |
| Citric Acid | 0.10 | 0.10 | 0.05 | 0.005 |
| Totals | 100.0 | 100.0 | 100.0 | 100.0 |
| IV of Fatty Acid | 18 | 55 | 47 | 56 |

(1)Di(soft tallowoyloxyethyl)dimethyl ammonium chloride where the fatty acyl groups of A have an IV of 18 and a cis/trans ratio of 70/30. B, C and D are derived from fatty acyl groups with IVs and cis/trans isomer ratios as outlined in Table I, Nos. 9 and 8, respectively.

EXAMPLE XIII

Example XIII is diester compound derived from fatty acid of Table I, No. 1, with an IV of 43 stored in molten form. These are relative measures of active based on HPLC. The initial ethanol level is approximately 12–13% in each sample. The sample containing 0.2% by weight water shows better storage stability at 3 weeks.

| | (150° F./66° C.) | |
|---|---|---|
| | Fresh Wt. % | 3 Wks Wt. % |
| Diester | 76 | 75 |
| Monoester | 8 | 9 |
| Water | 0.2 | 0.53 |
| Diester | 77 | 74 |
| Monoester | 9 | 10 |
| Water | 0.68 | 0.71 |

-continued

| | (150° F./66° C.) | |
|---|---|---|
| | Fresh Wt. % | 3 Wks Wt. % |
| Diester | 76 | 73 |
| Monoester | 9 | 12 |
| Water | 1.1 | 1.23 |
| Diester | 76 | 71 |
| Monoester | 9 | 12 |
| Water | 1.7 | 1.42 |

EXAMPLE XIV

| | Wt. % | Wt. % | Wt. % | Wt. % |
|---|---|---|---|---|
| Diester Compound[1] | 32 | 32 | 32 | 32 |
| Hydrochloric Acid | 0.04 | 0.04 | 0.04 | 0.01 |
| DC-2210 Antifoam (10%) | 0.10 | 0.10 | 0.10 | 0.10 |
| $CaCl_2$ | 0.75 | 0.75 | 0.75 | 0.80 |
| Coco Fatty Acid | 1.5 | 0.25 | 0.25 | — |
| Ethanol | 3.90 | 4.50 | 4.90 | 5.25 |
| Perfume | 1.35 | 1.35 | 1.35 | 1.35 |
| DI Water | 60.40 | 61.10 | 60.70 | 60.50 |

[1]Di(soft tallowoyloxyethyl)dimethyl ammonium chloride.

The above compositions are made by the following process:

1. Injecting the premix* into an acid water seat and milling at 70°–75° C.; adding 500 ppm of $CaCl_2$ at 70° C.; adding 3,500 ppm of $CaCl_2$ at 65° C.; adding perfume at 63° C.; and adding 3,500 ppm of $CaCl_2$ at 25° C.
2. Injecting the premix* into an acid water seat and milling at 70°–75° C.; adding 500 ppm of $CaCl_2$ at 70° C.; adding 3,500 ppm of $CaCl_2$ at 60° C.; adding 3,500 ppm of $CaCl_2$ at 24° C.; and adding perfume at 23° C.
3. Injecting the premix* into an acid water seat at 70°–75° C.; adding 500 ppm of $CaCl_2$ at 70° C.; adding 2,500 ppm of $CaCl_2$ at 40° C.; adding 4,500 ppm of $CaCl_2$ at 23° C.; milling at 22° C.; and adding perfume at 22° C.
4. Injecting the premix* into an acid water seat at 60° C.; adding 3,750 ppm of $CaCl_2$ at 40° C.; milling at 30° C.; adding 3,750 ppm of $CaCl_2$ at 23° C.; and adding perfume at 23° C.
5. Injecting the premix* into an acid water seat at 60° C.; adding 3,750 ppm of $CaCl_2$ at 40° C.; adding perfume and milling at 30° C.; and adding 3,750 ppm of $CaCl_2$ at 23° C.
6. Injecting the premix* into an acid water seat at 60° C.; adding 3,750 ppm of $CaCl_2$ at 40° C.; milling at 32° C.; adding perfume at 23° C.; and adding 3,750 ppm of $CaCl_2$ at 23° C.
7. Injecting the premix** into an acid water seat at 65° C.; adding 4,000 ppm of $CaCl_2$ at 40° C.; milling at 33° C.; adding perfume at 23° C.; and adding 4,000 ppm of CaCl at 23° C.

* The premix contains the active plus the ethanol plus coco fatty acid.
** The premix contains the active plus ethanol.

| Composition | Process Key | Initial Viscosity | Aged Viscosity | Dispersed Phase Volume |
|---|---|---|---|---|
| I | 1 | Cream | — | NA |
| II | 2 | 448 cp | — | NA |
| II | 3 | 143 cp | 390 cp | NA |

-continued

| Composition | Process Key | Initial Viscosity | Aged Viscosity | Dispersed Phase Volume |
|---|---|---|---|---|
| | | | (5 days) | |
| III | 4 | 58 cp | 333 cp (3 days) | 73–74% |
| III | 5 | 145 cp | 175 cp (13 days) | 71% |
| III | 6 | 125 cp | 162 cp (13 days) | 66–67% |
| IV | 7 | 112 cp | 125 cp (14 days) | 68% |

What is claimed is:

1. A quaternary ammonium compound having the structure:

$$(R)_{4-m}—N^+—[(CH_2)_n—Y—R^2]_m\ X^-$$

wherein each Y is —O—(O)C—;

m is 2 or 3;

n is 1 to 4;

each R is a $C_1$–$C_6$ alkyl group, benzyl group, or mixtures thereof;

each $R^2$ is a $C_{11}$–$C_{21}$ hydrocarbyl or substituted hydrocarbyl substituent; and $X^-$ is any textile softener-compatible anion;

wherein the compound is derived from $C_{12}$–$C_{22}$ fatty acyl groups having an Iodine Value of from greater than about 5 to less than about 100, a cis/trans isomer weight ratio of greater than about 30/70 when the Iodine Value is less than about 25, the level of unsaturation of the fatty acyl groups being less than about 65% by weight, wherein said compounds are capable of forming concentrated aqueous compositions with concentrations greater than about 13% by weight at an Iodine Value of greater than about 10 without viscosity modifiers other than normal polar organic solvents present in the raw material of the compound or added electrolyte, and wherein any fatty acyl groups from tallow must be hydrogenated and/or deodorized.

2. The compound according to claim 1 wherein the Iodine Value is from about 10 to about 65 and the cis/trans isomer weight ratio is greater than about 50/50 when the Iodine Value is less than about 25.

3. The compound according to claim 2 wherein the Iodine Value is from about 20 to about 60 and the cis/trans isomer weight ratio is greater than about 70/30 when the Iodine Value is less than about 25.

4. The compound according to claim 1 wherein $R^2$ is derived from fatty acid containing at least 90% $C_{16}$–$C_{18}$ chainlength.

5. The compound according to claim 4 wherein the Iodine Value is from about 10 to about 65 and the cis/trans isomer weight ratio is greater than about 50/50 when the Iodine Value is less than about 25.

6. The compound according to claim 5 wherein the Iodine Value is from about 20 to about 60 and the cis/trans isomer weight ratio is greater than about 70/30 when the Iodine Value is less than about 25.

7. A quaternary ammonium compound having the structure:

$$(R)_{4-m}—N^+—[(CH_2)_n—Y—R^2]_m\ X^-$$

wherein each Y is —O—(O)C—;

m is 2 or 3;

n is 1 to 4;

each R is a $C_1$–$C_6$ alkyl group, benzyl group, or mixtures thereof;

each $R^2$ is a $C_{11}$–$C_{21}$ hydrocarbyl or substituted hydrocarbyl substituent; and $X^-$ is any textile softener-compatible anion;

wherein the compound is derived from $C_{12}$–$C_{22}$ fatty acyl groups having an Iodine Value of from greater than about 20 to less than about 100 for optimum static control, the level of unsaturation of the fatty acyl groups is less than about 65% by weight, wherein said compounds are capable of forming concentrated aqueous compositions with concentrations greater than about 13% by weight without viscosity modifiers other than normal polar organic solvents present in the raw material of the compound or added electrolyte, and wherein any fatty acyl groups from tallow must be modified.

8. The compound according to claim 7 wherein the Iodine Value is from about 20 to about 65.

9. The compound according to claim 8 wherein the Iodine Value is from about 40 to about 60.

10. The compound according to claim 9 wherein the compound is derived from methyl diethanolamine, fatty acid, and methyl chloride.

11. The compound according to claim 7 wherein $R^2$ is derived from fatty acid having at least 90% $C_{16}$–$C_{18}$ chainlength.

12. The compound according to claim 11 wherein the cis/trans isomer weight ratio is greater than about 80/20.

13. The compound according to claim 12 wherein the Iodine Value is from about 20 to about 65.

14. The compound according to claim 13 wherein the Iodine Value is from about 40 to about 60.

15. The compound according to claim 14 wherein the level of polyunsaturates is less than about 5%.

16. The compound according to claim 15 wherein the compound is derived from methyl diethanolamine, fatty acid, and methyl chloride.

17. A quaternary ammonium compound having the structure:

$$(R)_{4-m}—N^+—[(CH_2)_n—Y—R^2]_m\ X^-$$

wherein each Y is —O—(O)C—;

m is 2 or 3;

n is 1 to 4;

each R is a $C_1$–$C_6$ alkyl group, benzyl group, or mixtures thereof;

each $R^2$ is a $C_{11}$–$C_{21}$ hydrocarbyl or substituted hydrocarbyl substituent; and $X^-$ is any textile softener-compatible anion; wherein the compound is derived from $C_{12}$–$C_{22}$ fatty acyl groups having an Iodine Value of from greater than about 5 to less than about 25 for optimum low temperature stability, and the cis/trans isomer weight ratio is greater than about 30/70.

18. The compound according to claim 17 wherein the Iodine Value is from about 10 to about 25 and the cis/trans isomer weight ratio is greater than about 50/50.

19. The compound according to claim 18 wherein the Iodine Value is from about 15 to about 20 and the cis/trans isomer weight ratio is greater than about 70/30.

20. The compound according to claim 17 wherein $R^2$ is derived from fatty acid having at least 90% $C_{16}$–$C_{18}$ chainlength.

21. The compound according to claim 20 wherein the Iodine Value is from about 10 to about 25 and the cis/trans isomer weight ratio is greater than about 50/50.

22. The compound according to claim 21 wherein the Iodine Value is from about 15 to about 20 and the cis/trans isomer weight ratio is greater than about 70/30.

23. The compound according to claim 22 wherein the polyunsaturation content of the fatty acyl group is less than about 1%.

24. The compound according to claim 23 wherein the compound is derived by mixing hardened fatty acid with unsaturated fatty acid which is hydrogenated to remove polyunsaturation while maintaining cis/trans isomer weight ratios of greater than about 30/70.

* * * * *